(12) United States Patent
Adamiec

(10) Patent No.: US 10,034,701 B2
(45) Date of Patent: Jul. 31, 2018

(54) SINGLE PROCEDURE TORQUE LIMITER

(71) Applicant: Greatbatch Ltd., Clarence, NY (US)

(72) Inventor: John William Adamiec, Warsaw, IN (US)

(73) Assignee: Greatbatch Ltd., Clarence, NY (US)

( * ) Notice: Subject to any disclaimer, the term of this patent is extended or adjusted under 35 U.S.C. 154(b) by 318 days.

(21) Appl. No.: 14/875,299

(22) Filed: Oct. 5, 2015

(65) Prior Publication Data

US 2016/0095641 A1   Apr. 7, 2016

Related U.S. Application Data

(60) Provisional application No. 62/059,414, filed on Oct. 3, 2014.

(51) Int. Cl.
*A61B 17/88* (2006.01)
*B25B 23/14* (2006.01)
*B25B 23/142* (2006.01)
*A61B 90/00* (2016.01)

(52) U.S. Cl.
CPC ........ *A61B 17/8875* (2013.01); *B25B 23/141* (2013.01); *B25B 23/1427* (2013.01); *A61B 2090/031* (2016.02)

(58) Field of Classification Search
CPC ................................................ A61B 17/8875
See application file for complete search history.

(56) References Cited

U.S. PATENT DOCUMENTS

| | | | |
|---|---|---|---|
| 3,367,456 A | 2/1968 | Bohnhoff | |
| 4,746,320 A | 5/1988 | Kilwin | |
| 5,630,490 A | 5/1997 | Hudson et al. | |
| 7,318,776 B2 | 1/2008 | Honda | |
| 2009/0293687 A1 | 12/2009 | Nino et al. | |
| 2012/0198972 A1* | 8/2012 | Nino ........................ | B25B 15/04 81/471 |
| 2013/0226192 A1 | 8/2013 | Nino et al. | |

* cited by examiner

*Primary Examiner* — Andrew Yang
(74) *Attorney, Agent, or Firm* — Michael F. Scalise

(57) ABSTRACT

A torque limiting tool is described. The tool comprises a torque limiting mechanism that drives a shank about a rotational axis. The torque limiting mechanism comprises a plurality of opposed first and second gears having a plurality of outwardly extending first and second gear prongs. The plurality of first and second gear prongs extends outwardly at an inclined angle along an intermediate prong portion from a prong proximal end positioned along the disc sidewall surface to a prong distal portion. Each of the prong distal portions comprises a plateau portion that extends about parallel with the disc sidewall surface and resides at a distance away from the sidewall surface of the respective first and second discs. The mechanism is constructed such that toque is transferred therebetween when the respective intermediate portions of the opposed first and second prongs are in physical contact. When an upper torque limit is exceeded, either of the respective first and second prongs deflect, thus causing the other of the first or second prong to ride along the deflected ramp surface of the intermediate prong portion until the first and second prongs disengage.

33 Claims, 8 Drawing Sheets

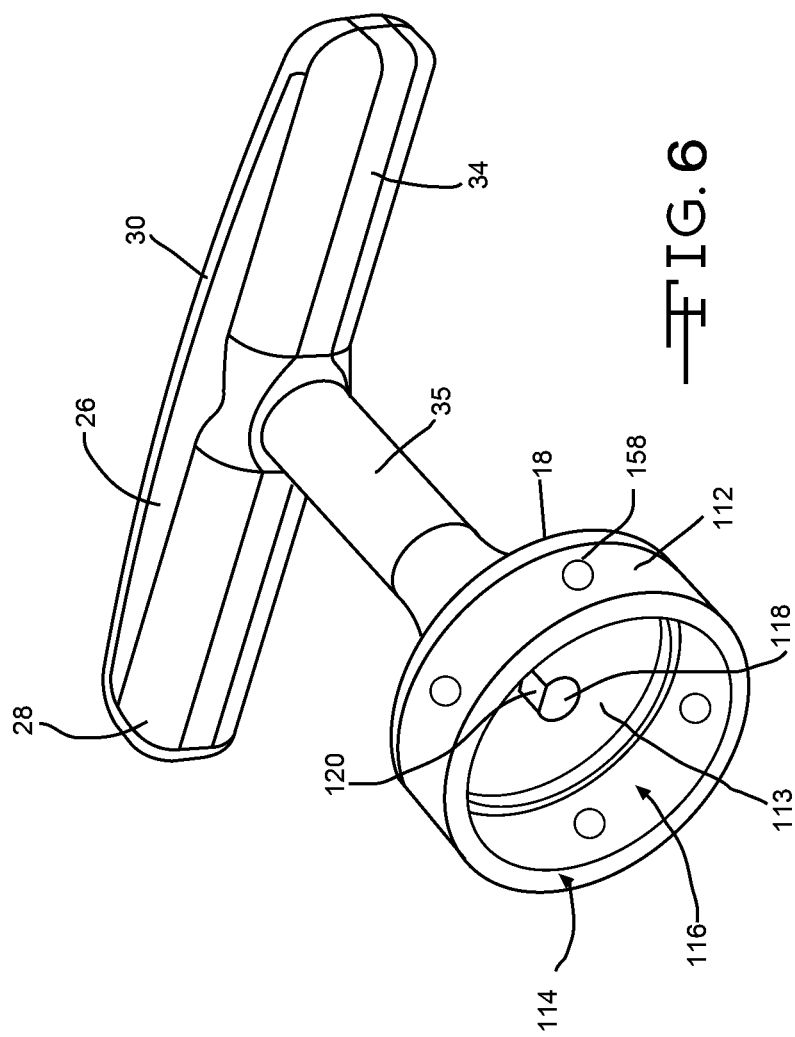

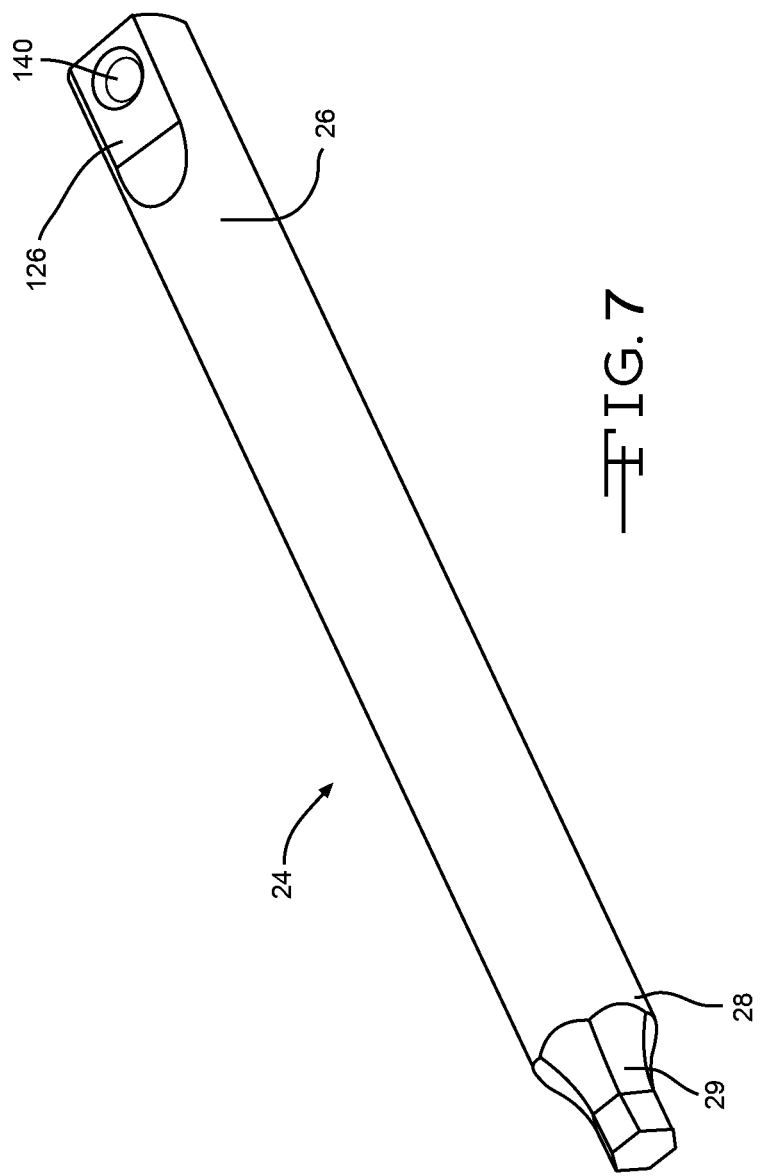

SINGLE PROCEDURE TORQUE LIMITER

CROSS REFERENCE TO RELATED APPLICATION

This application claims priority from U.S. Provisional Application Ser. No. 62/059,414, filed Oct. 3, 2014.

TECHNICAL FIELD

This invention relates to the art of instruments used in orthopedic surgical procedures. More specifically, this invention relates to a torque limiting tool that is used to tighten a fastener during orthopedic surgical procedures.

BACKGROUND OF THE INVENTION

Torque limiting tools are extensively used to tighten a fastener to a specific torque. Such tools are extensively used during surgical procedures, such as an orthopedic surgical procedure. For example, a torque limiting tool may be used to tighten a fastener that is used to secure an orthopedic implant or bone plate. As such, it is often important that the fastener is tightened to a specific torque. Over tightening a fastener could result in damage to the orthopedic implant or bone plate. Likewise, a fastener that is not adequately tightened, may result in undesirable movement of the implant or bone plate within the patient. Such movement of the orthopedic implant or bone plate may be adverse to a patient as the implant may move to a position that is not efficacious to the patient.

Orthopedic bone plates play a critical role in the healing process of broken bones. Once a bone has been fragmented, it is often ideal for the broken bone fragments to be joined back together under compression to promote improved healing. The bone plate is a critical device that is used as a stabilizing bar that bridges the gap in bringing the bone fragments together.

During surgery, a bone plate is inserted next to the fragmented bone of a patient. Various compression and locking screws are typically placed through the bone plate to thus anchor the bone fragments together. They are then anchored into each of the bone fragments and tightened, pulling the bone fragments together under a compression load. Once the compression screws are set in place, locking bone screws are inserted through the bone plate and anchored into the fragmented bone. The locking bone screws in conjunction with the bone plate secure the bone fragments together and ensure that they do not move. Therefore, it is important that the compression and locking screws are tightened to a specific torque to ensure that the bone plate is securely in place, thus minimizing the possibility of causing further damage.

The medical industry has made use of both reusable and single use torque limiting tools. As previously mentioned, it is important that the torque limiting tool, regardless of whether it is designed to be reusable or for single use, be capable of imparting a precise amount of torque. Reusable torque limiting tools require frequent recalibration to ensure a precise amount of torque is imparted by the tool. Recalibration is a cumbersome process that must be performed routinely to ensure the tool operates correctly.

Single use torque limiting tools are easy to use and are a reliable alternative to a reusable tool. A single use torque limiting tool may be packaged with each implant and be specifically designed according to the implant's specifications. Once the tool has been used, it can be discarded, thus ensuring the torque limiting tool will impart a precise amount of torque that is required to secure the implant.

The present invention provides a single use torque limiting tool having an improved torque limiting mechanism that ensures the application of a precise amount of torque. Unlike prior art torque limiting tools, such as the torque limiting device disclosed by Nino et al. in U.S. patent application publication number 2009/0293687, the torque limiting tool of the present invention does not comprise a bias member or a plurality of washers to establish a torque limit. In contrast, the torque limiting mechanism of the present invention comprises two opposing gears, each of which has a plurality of outwardly extending prongs having an angular orientation with opposing ramp surfaces. Torque is thus transferred between the gears when at least two of the opposing prongs are in physical contact therebetween.

More specifically, the prongs of the gears of the torque limiting mechanism of the present invention are positioned such that the respective prong ramp surfaces are positioned in opposition to each other. Torque is transferred between the gears when the opposing prongs physically contact therebetween. However, once a maximum amount of torque is exceeded, the prongs of the opposing gears disengage. Specifically, either of the prongs of the opposing gears flex towards the respective gear surface, thereby enabling the opposing prongs to slide off the ramp surface, thus disengaging the gears and preventing torque transfer between the gears.

Therefore, in addition to the structural differences between the torque limiting device of Nino and other prior art devices, the amount of torque imparted by the present invention is limited by the mechanical properties of the prong. More specifically, in contrast to prior art devices, the amount of torque imparted by the tool of the present invention is limited by the ability of the respective prongs to resist mechanical flexure.

SUMMARY OF THE INVENTION

The present invention provides a torque limiting tool that is designed to impart a specific amount of torque. More specifically, the torque limiting tool of the present invention is preferably designed to tighten a fastener, such as a fastener used to secure an orthopedic implant or bone plate, to a specific torque loading.

The torque limiting tool comprises a torque limiting mechanism having opposed first and second gears that mate together to drive a shank located at the distal tool end. Each of the opposed gears comprises an annular disc having a plurality of prongs that outwardly extend from the disc sidewall surface. In addition, a bushing, having a bushing height, is positioned between the opposing gears. The height and position of the bushing establishes the point of contact between the opposing gear prongs.

Each of the plurality of opposing prongs outwardly extends from the gear sidewall surface. In a preferred embodiment, each of the plurality of prongs is oriented at an angular relationship with respect to the gear sidewall surface. This angular orientation of the prongs helps enable each prong to independently flex in either an upwardly or downwardly direction with respect to the sidewall surface.

In addition, each of the plurality of prongs comprises a proximal prong end that extends from the gear sidewall surface to a distal prong portion along an intermediate prong portion having a ramp surface. The distal prong portion preferably comprises a plateau portion having a surface that extends about parallel to the gear sidewall surface.

Torque is transferred between the opposing gears when the angled prongs of the respective opposing first and second gears are in physical contact therebetween. In a preferred embodiment, torque is transferred between the opposing gears when at least a portion of the opposing inclined prong surfaces are physically in contact therebetween. Once a maximum torque limit is exceeded, one of the opposing prongs flexes towards the respective gear sidewall surface, thus enabling the other of the opposing prongs to ride along the opposed ramp surface until the opposing prongs separate, thereby disengaging the prongs and preventing torque to be imparted by the tool.

The maximum amount of torque imparted by the tool is established by either of the opposing prong's ability to resist mechanical flexure. This is influenced by the combination of the height of the bushing positioned between the opposing gears and the material composition of the gears. The height of the bushing helps establish the point of contact between the prongs of the opposing gears. This influences the amount of friction between the opposing prongs, and thus, the amount of force, i.e., torque required to deflect the opposing prongs. For example, a bushing having a relatively short height creates a point of contact closer to the base of the prongs, thus requiring the application of an increased amount of torque to separate the opposing prongs.

In addition, the maximum torque imparted by the tool is influenced by the material of which the gears are constructed. Material selection can have a direct effect on the flexural movement of the gear prongs as different materials have differing mechanical properties. For example, materials having an increased modulus of elasticity tend to exhibit a greater mechanical stiffness, thereby requiring the application of a greater force to bend or flex the material. Therefore, constructing the gears of a material having a greater modulus of elasticity requires the application of an increased amount of force to flex and separate the respective gear prongs, thus increasing the amount of torque imparted by the tool. These and other additional unique structural features of the torque limiting tool will be discussed in further detail.

BRIEF DESCRIPTION OF THE DRAWINGS

FIG. 6 shows a perspective view of an embodiment of the proximal housing portion.

FIG. 7 is a perspective view of an embodiment of the shank utilized in the torque limiting tool of the present invention.

DETAILED DESCRIPTION OF THE PREFERRED EMBODIMENT

Figure 1:
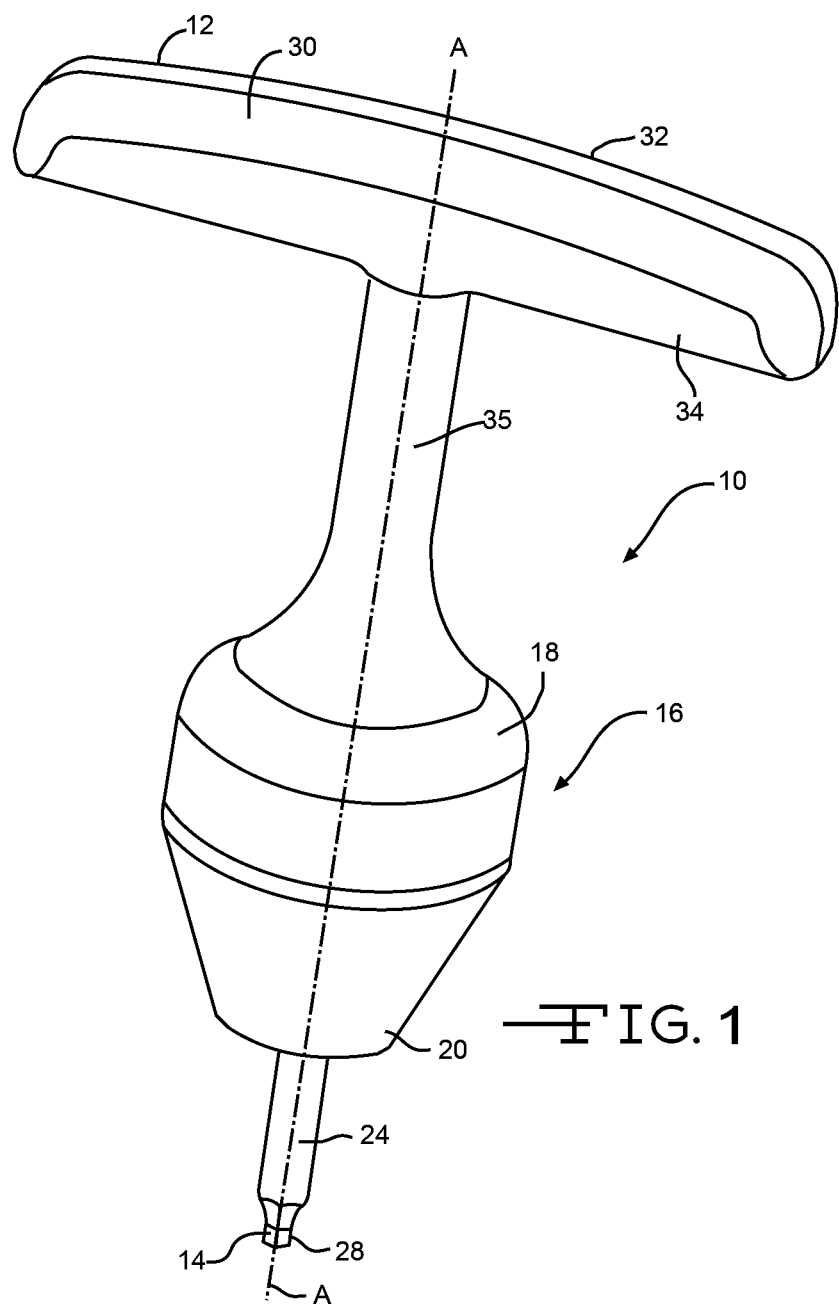
FIG. 1 illustrates a perspective view of an embodiment of the torque limiting tool of the present invention.
Figure 4:
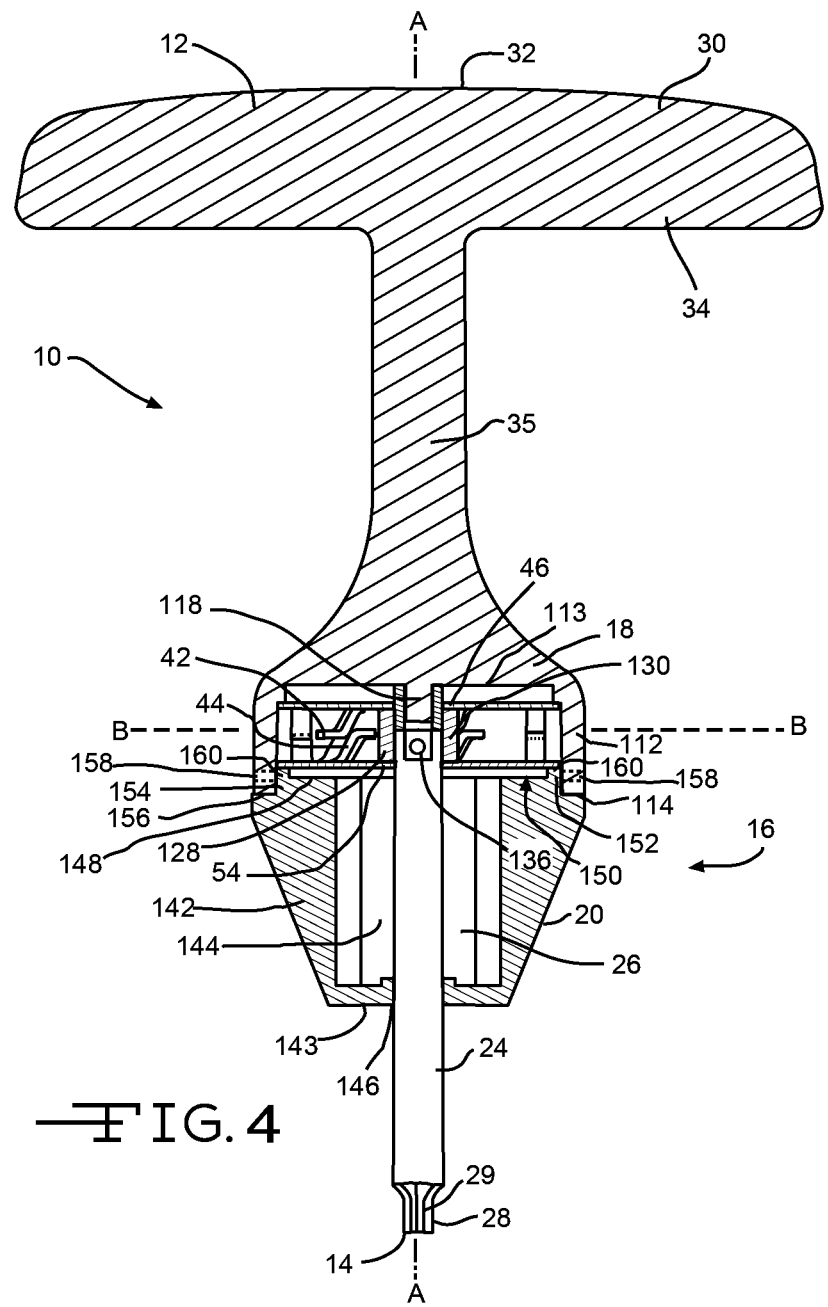
FIG. 4 is a cross-sectional view of the torque limiting tool illustrated in FIG. 1.

Now turning to the figures, FIGS. 1 and 4 illustrate a preferred embodiment of a torque limiting tool 10 of the present invention. As shown, the tool 10 has a tool proximal end 12 spaced from a tool distal end 14 that extends along longitudinal axis A-A. As shown, the tool 10 comprises a housing 16 having spaced apart proximal and distal housing portions 18, 20. In addition, the torque limiting tool 10 comprises a torque limiting mechanism 22 (FIG. 2) disposed within the housing 16. A shank 24 (FIG. 7) having spaced apart proximal and distal shank ends 26, 28 extends distally along longitudinal axis A-A from within the housing 16. As will be described in more detail, the mechanism 22 engages the proximal shank end 26 and limits the maximum amount of torque that can be applied thereto. As defined herein, torque is a twisting force that tends to cause rotation. More specifically, torque is a measure of a force's tendency to produce rotation about an axis that is equal to the product of the force vector and the radius vector from the axis of rotation to the point of application of the force.

FIG. 1 illustrates a perspective view of the torque limiting tool 10 of the present invention. As shown, the tool has a handle portion 30 that resides at a housing proximal end 32. In a preferred embodiment, the handle portion 30 is of a "T" shape having a handle bar 34 that extends about perpendicular to a handle shaft 35. The shaft 35 extends axially along a longitudinal axis A-A.

The shank 24 extends lengthwise along longitudinal axis A-A from the shank proximal end 26 disposed within the housing 16 to the shank distal end 28 that resides external of the distal housing portion 20. The shank distal end preferably comprises a bit 29 that is designed to engage with a fastener (not shown). The bit 29 may be constructed of a plurality of unlimited geometries, examples of which may include, but are not limited to, a slotted end, a Phillips® end, a Torx® end, a clutch end, or a Pozidriv® end. In a preferred embodiment, the shank 24 rotates about longitudinal axis A-A which serves as the rotational axis thereof.

Figure 2:
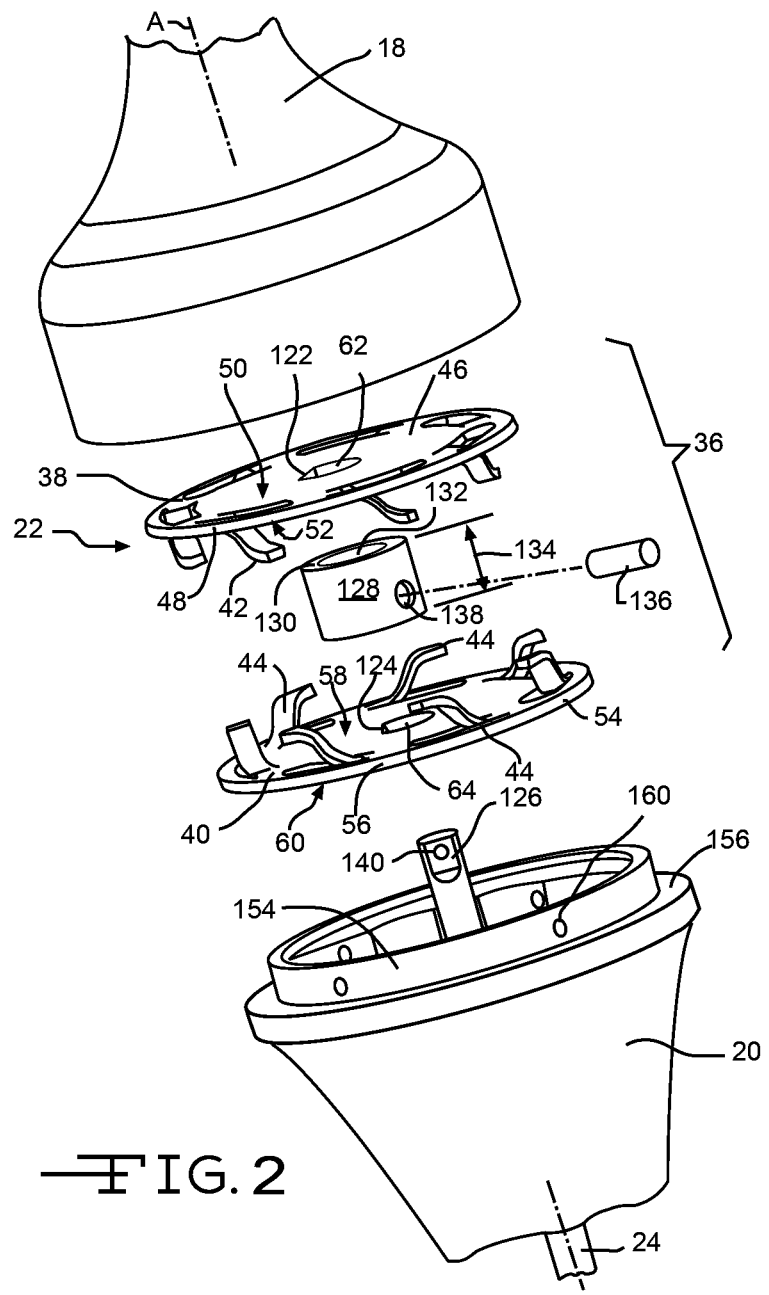
FIG. 2 shows a magnified view of an embodiment of the torque limiting mechanism of the present invention.

FIG. 2 shows a magnified view of the torque limiting mechanism 22 of the present invention. As illustrated, the mechanism 22 comprises a clutch 36 having spaced apart and opposing first and second gears 38, 40. The first gear 38 is positioned proximal to the second gear 40. As illustrated, each of the first and second gears 38, 40 comprises a plurality of outwardly extending gear prongs. The first gear 38 comprises a plurality of first prongs 42 that outwardly extend from the first disc sidewall surface in a distal direction away from the handle 30. The second gear 40 comprises a plurality of second prongs 44 that outwardly extend from the second disc sidewall surface in a proximal direction toward the handle 30. In a preferred embodiment, torque is imparted to the shank 24, thereby causing it to rotate about longitudinal axis A-A, when at least a portion of one of the first prongs 42 of the first gear 38 comes into physical contact with at least a portion of one of the plurality of second prongs 44 of the second gear 40. As will be discussed in more detail, when a maximum torque is exceeded, the at least first prong 42 of the first gear 38 separates from the at least second prong 44 of the second gear 40, thus, disengaging the gears thereby preventing further rotation of the shank 24 about longitudinal axis A-A.

As illustrated in FIG. 2, the first gear 38 comprises a first disc 46 having an annular shape. The first disc 46 has a first disc thickness 48 that extends along longitudinal axis A-A between opposed top and bottom first disc sidewall surfaces 50, 52. The plurality of first prongs 42 extends outwardly from the bottom sidewall surface 52 of the first gear 38. Similar to the first gear 38, the second gear 40 comprises a second disc 54 having an annular shape. The second disc 54 comprises a second disc thickness 56 that extends along longitudinal axis A-A between opposed top and bottom second disc sidewall surfaces 58, 60. The plurality of second prongs 44 extends outwardly from the second disc top sidewall surface 58. The first and second prongs 42, 44 are preferably positioned facing each other within the mechanism 22.

In addition, a throughbore extends through the disc thickness of each of the gears. As shown, a first throughbore 62 extends along longitudinal axis A-A through the first disc thickness 48 and a second throughbore 64 extends along longitudinal axis A-A through the second disc thickness 56. The first throughbore 62 provides a means by which the first gear 38 is connected to the proximal housing portion 18 and the second throughbore 64 provides a means by which the shank 24 is connected to the second gear 40.

In a preferred embodiment the housing 16 is composed of a polymeric material. In addition, the first and/or second gears 38, 40 may be composed of a polymeric material. Such materials may include but are not limited to thermoplastics such as acrylics, acrylonitrile butadiene styrene (ABS), poly(hexamethylene adipamide), polylactic acid, polybenzimidazole, polycarbonate, polyether sulfone, poly ether ether ketone (PEEK), polyetherimide, polyethylene, polyphenylene oxide, polyphenylene sulfide, polypropylene, polystyrene, polyvinyl chloride, and combinations thereof. Such polymeric materials provide a durable structure and allow for flexure of the gear prongs. Alternatively, the housing 16 and/or the first and second gears 38, 40 may be constructed of a metallic material such as various stainless steel alloys, a ceramic material, such as a stainless steel alloy, or combinations thereof.

In a preferred embodiment, the maximum torque limit of the tool 10 can be adjusted to a specific torque value by constructing the first and second gears 38, 40 of materials having a different modulus of elasticity. For example, the amount of torque imparted by the tool 10 can be increased by constructing the first and second gears 38, 40 of materials having a relatively high modulus of elasticity. Likewise, the amount of torque can be decreased by constructing the first and second gears 38, 40 of a material having a relatively low modulus of elasticity. Non-limiting examples of materials that have a relatively "low" modulus of elasticity may include, but are not limited to, rubber and low density polyethylene having modulus of elasticity's ranging from about 0.01 GPa to about 1.0 GPa. Non-limiting examples of materials having a relatively "medium" modulus of elasticity may include, but are not limited to, polypropylene, polyethylene terephthalate (PET), nylon and polystyrene having a modulus of elasticity ranging from about 1.0 GPa to about 4.0 GPa. Non-limiting examples of relatively "high" modulus of elasticity generally comprise those materials having a modulus of elasticity greater than 4.0 GPa. The first or second disc are composed of a material having a modulus of elasticity ranging from about 0.01 GPa to about 10 GPa, more preferably from about 0.5 GPa to about 5 GPa. As defined herein modulus of elasticity is a mechanical property of linear elastic solid materials. Modulus of elasticity is the force (per unit area) that is required to stretch (or compress) a material sample. In a preferred embodiment, the torque limiting tool can be design to apply a maximum torque from about 0.007 N-m (1 oz. per in) to about 122 N-m (90 lbf).

Figure 3:
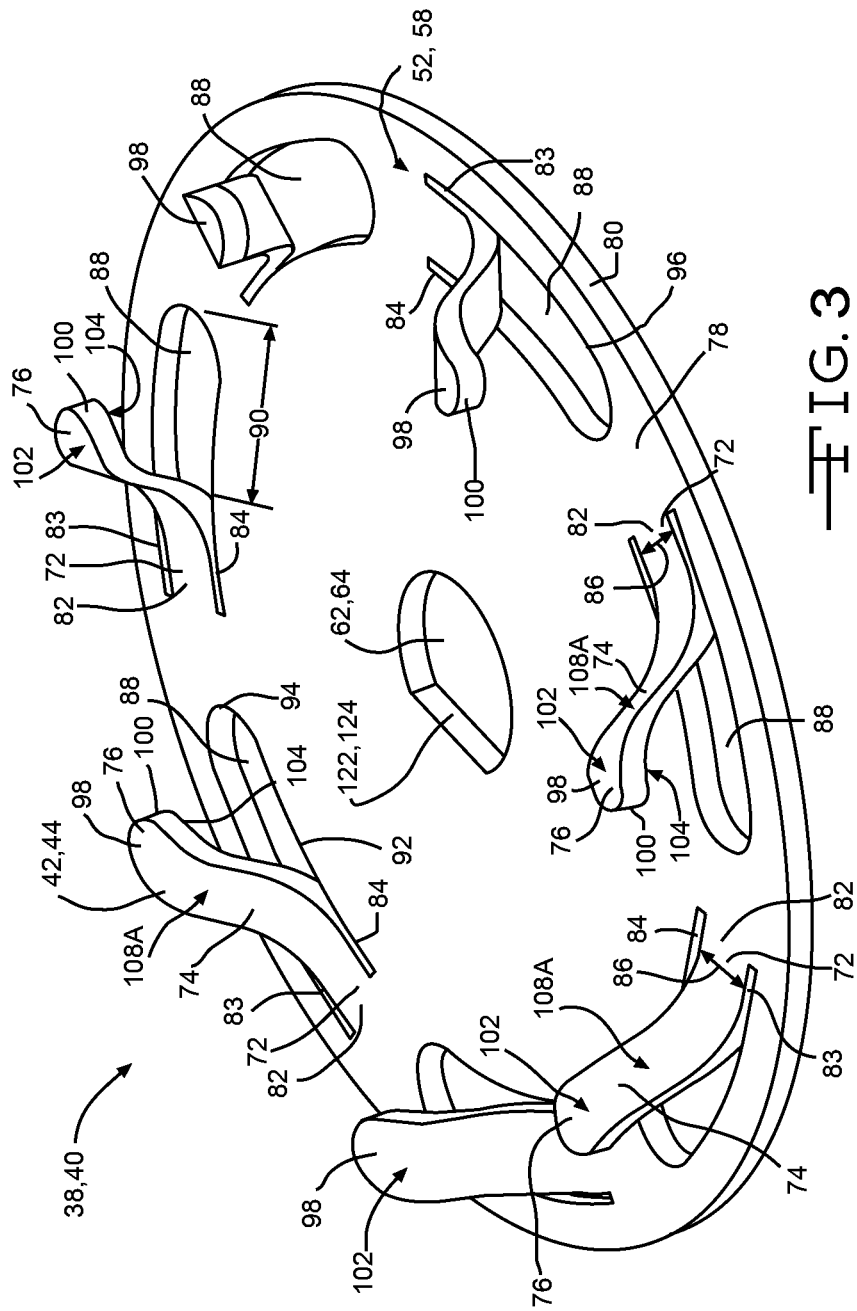
FIG. 3 illustrates a magnified view of an embodiment of a gear that is utilized in the torque limiting mechanism.

FIG. 3 illustrates a magnified view of the embodiment of the first and second gear 38, 40 utilized within the torque limiting mechanism 22 of the present invention. It is noted that the embodiment of the gear illustrated in FIG. 3 is representative of both the first and second gears 38, 40 that comprise the torque limiting mechanism 22 of the present invention. In a preferred embodiment, the first and second gears 38, 40 are of a similar structure in that both comprise an annular disc shape having a plurality of prongs that extend outwardly from the respective disc sidewall surface. In addition, each of the prongs 38, 40 comprises a prong thickness 66 (FIGS. 5 and 5A) that extends between opposing first and second prong surfaces 68, 70. In a preferred embodiment, the prong thickness 66 may be about equal to the thickness of the respective first or second disc 46, 54. Each prong 42, 44 is preferably cut from the disc sidewall and comprises a proximal prong end 72 that extends along an intermediate prong portion 74 having a ramp surface to a distal prong portion 76. As illustrated in FIGS. 2, 3, 5, 5A and 5B, the distal portions of each of the plurality of first and second prongs 42, 44 reside at a distance away from the sidewall surface of the respective first and second discs 46, 54. This outwardly extending prong orientation helps enable flexure of the plurality of first and second prongs 42, 44 with respect to the disc sidewall.

In addition, the plurality of first and second prongs 42, 44 are preferably positioned circumferentially about longitudinal axis A-A of the first and second discs, respectively. More specifically, the plurality of first and second prongs 42, 44 are positioned annularly around longitudinal axis A-A and spaced inwardly from an outer disc edge 80 along the outer disc perimeter 78. In addition, each of the prongs 42, 44 is preferably oriented with its distal prong end 76 facing towards, but spaced from the proximal prong end 72 of an adjacent prong. Furthermore, each of the plurality of first and second prongs 42, 44 is preferably positioned from about 0.1 cm to about 5.0 cm from the outer edge 80 of the annular disc (FIG. 3).

In a preferred embodiment, the first and second gear prongs 42, 44 are positioned having about the same orientation about the first and second discs, respectively. For example, from a perspective of looking at surfaces 52, 58 of the respective discs 46, 54, each of the plurality of first and second prongs 42, 44 may be oriented in a clockwise direction with respect to longitudinal axis A-A, as illustrated in FIG. 3, or alternatively, each of the plurality of first and second prongs 42, 44 may be oriented in a counterclockwise direction with respect to longitudinal axis A-A. This preferred orientation of the plurality of first and second prongs 42, 44 ensures that the prongs are positioned in a directly opposed mirror plane orientation when constructed in the mechanism 22. Furthermore, as illustrated in FIGS. 2, 3, 5A, and 5B, this preferred orientation ensures physical contact of the inclined intermediate portions 74 of the plurality of first and second prongs 42, 44, respectively.

Even though the prongs may be oriented in either a clockwise or counterclockwise orientation, it's important that both the first and second gears 38, 54 have the same prong orientation for a particular torque limiting tool. Again, that is with respect to a perspective of looking along axis A-A at the respective surfaces 52, 58 of discs 46, 54.

The torque limiting mechanism 22 of the present invention is constructed such that each of the plurality of first and second prongs 42, 44 is capable of independent flexural movement. In a preferred embodiment, each of the prongs 42, 44 acts as a cantilever beam with respect to the disc sidewall. As illustrated in FIGS. 3, 5, 5A, and 5B, the prong proximal end 72 is physically connected to the first or second disc, respectively, thus forming a prong flexure location 82 therebetween. More specifically, the proximal prong end 72 is an extension of the disc sidewall. As illustrated, the disc 46, 54 uniformly transitions to the proximal prong portion at the flexural location 82 of the proximal prong end 72.

As shown, left and right slots 83, 84 extend through the thickness of the disc 46, 54 along respective left and right prong sides to define a prong width 86 therebetween. The respective left and right slots 83, 84 extend through the thickness of the disc 46, 54. Furthermore, the prong width 86 may range from about 0.1 cm to about 5 cm. In a preferred embodiment, the flexure location 82 enables flexure of the prong in either an upwardly or downwardly direction with respect to the disc sidewall surface 50, 52, 58, 60 of the first or second disc, respectively.

As illustrated, the left and right slots 83, 84 meet a disc opening 88 positioned beneath each of the outwardly extending prongs 42, 44. In a preferred embodiment, the disc opening 88 has an opening length 90 that extends from an opening proximal end 92 to a distal end 94. As illustrated, each of the disc openings 88 has an opening perimeter 96. In a preferred embodiment, flexure of the prong 42, 44 may cause at least a portion of the first or second prong 42, 44 to deflect, at least partially, within the disc opening 88, but without contacting the perimeter 96.

In a preferred embodiment, the distal prong portion 76 comprises a prong plateau 98 that extends to a prong distal end 100. In a preferred embodiment, the prong plateau portion 98 comprises opposed top and bottom plateau portion surfaces 102, 104 that are orientated about perpendicular to longitudinal axis A-A. As illustrated in FIGS. 3, 4, 5, 5A, and 5C, in a preferred embodiment the top plateau surface 102 extends along imaginary plane B-B parallel to imaginary plane C-C that extends along the top sidewall surface 58 of the second disc 56 or imaginary plane D-D which extends along the bottom sidewall surface 52 of the first disc 46. In a preferred embodiment, a prong distal end offset distance 106 aligned generally parallel to axis A-A extends between imaginary planes B-B and C-C or between imaginary planes B-B and D-D. In a preferred embodiment, the prong plateau 98 is positioned about 0.1 cm to about 5 cm away from the disc sidewall surface.

Figure 5:
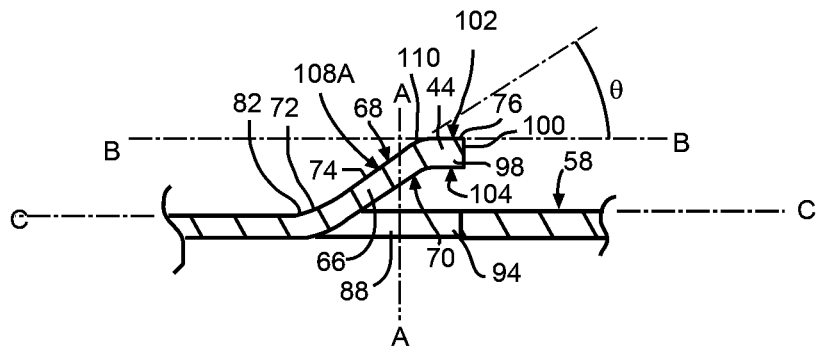
FIG. 5 is a magnified cross-sectional view of a gear prong of the present invention.

As illustrated in FIGS. 2, 3, 5, 5A, and 5B, the intermediate prong portion 74 is oriented at an angular relationship with respect to imaginary plane B-B. In a preferred embodiment, as illustrated in FIG. 5, the intermediate prong portion 74 is positioned at an angle θ of between about 40° to about 50° with respect to the top sidewall surface 68 of the intermediate portion 74 and imaginary plane B-B which extends about parallel to the top sidewall surface 58. This angular orientation of the intermediate portion 74 provides a ramp surface 108A that extends along top intermediate sidewall surface 68 to an inflection point 110 positioned between the distal end of the intermediate portion 74 and the prong plateau proximal end 100. The angular orientation and ramp surface 108A of the intermediate portion 74 enable flexural movement of the prong 42, 44 with respect to the disc sidewall surface 52, 60.

Figure 5A:
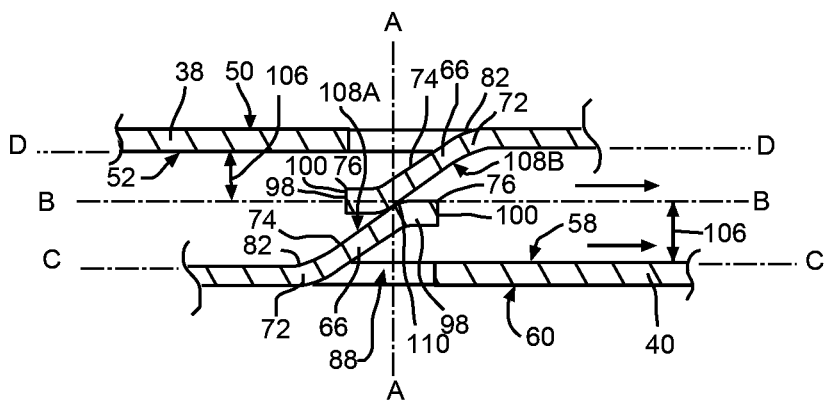
FIG. 5A illustrates a cross-sectional view showing an embodiment of the engagement between the first and second gears of the torque limiting mechanism.
Figure 5B:
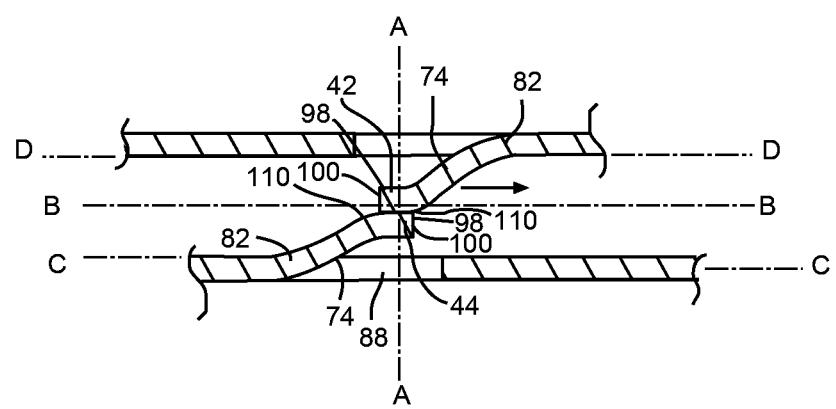
FIG. 5B illustrates a cross-sectional view showing an embodiment of the first and second gears of the torque limiting mechanism in a disengaged orientation.

FIG. 5A illustrates an embodiment of the engagement between the first and second gears. As shown, the first ramp surface 108A of the intermediate portion 74 of the second prong 44 is in physical contact with a second ramp surface 108B of the opposing intermediate portion 74 of the first prong 42. The physical contact therebetween causes rotation of the second prong 44 which in turn causes rotation of the second disc and the shank 24. However, when a torque that exceeds a torque upper limit is applied to the first gear, as illustrated in FIG. 5B, the force causes the second prong 44 of the second gear to deflect. This therefore, enables the second ramp surface 108B of the first prong 42 to ride along the deflected first ramp surface 108A until the opposing prongs 42, 44 separate.

FIG. 6 illustrates an embodiment of the proximal housing portion 18 (FIGS. 2 and 4). As illustrated, an annular sidewall 112 extends parallel to longitudinal axis A-A from a distal edge 114 to an end wall 113. End wall 113 in turn forms into the shaft 35 of handle 30. The annular sidewall 112 defines a proximal portion housing cavity 116 within which a portion of the torque limiting mechanism is disposed.

In addition, a post 118 extends outwardly along longitudinal axis A-A from the end wall 113 of the proximal housing portion 18. In a preferred embodiment, the post 118 is positioned through the first throughbore 62 of the first annular disc 46 securing the first disc 46 thereto. The first prongs 42 of the first gear 38 are positioned extending in a distal direction away from the handle 30.

In a preferred embodiment, the outer circumference of the post 118 comprises a flat portion 120 that mates with a corresponding disc throughbore flat portion 122 (FIG. 3). The mating of the two respective flat portions 120, 122 thus provides a secure connection between the first disc 46 and the proximal housing portion 18. Alternatively, the post 118 and corresponding first disc throughbore 62 may be constructed having a cross-sectional geometry of a multiple of non-limiting shapes. This helps ensure torque transfer between the handle 30 and the first disc 46 about longitudinal axis A-A.

As illustrated in FIG. 4, the opposing second gear 40 is secured to the proximal end 26 of the shank 24. More specifically, the proximal shank end 26 is positioned through the second throughbore 64 that extends through the second disc thickness 56 along longitudinal axis A-A. In a preferred embodiment, the diameter of the second throughbore 64 comprises a flat portion 124 (FIG. 3) that mates with a corresponding chamfer portion 126 (FIG. 2) that resides at the proximal end 26 of the shank 24 (FIG. 7). In a preferred embodiment the chamfered portion 126 of the shank proximal end 26 is positioned through the second througbore 64 such that they mate therebetween. This ensures that a maximum amount of torque is applied to the shank 24 about longitudinal axis A-A. Alternatively, the proximal shank end 26 and corresponding second throughbore 64 may be constructed having a cross-sectional geometry of a multiple of non-limiting shapes.

A bushing 128 serving as a spacer (FIG. 2) may also be used to help secure the second annular disc 54 to the proximal shank end 26. In a preferred embodiment illustrated in FIG. 2, the bushing 128 comprises an annular sidewall 130 that defines an opening 132 extending along axis A-A through a bushing height 134. In a preferred embodiment, the proximal shank end 26 is positioned at least partially through the bushing opening 132. A pin 136 is positioned through a side opening 138 of the sidewall 130 and through a proximal shank opening 140 that extends about perpendicular through the diameter of the shank 24. The second annular disc 54 is positioned about the circumference of the shank 24 such that the plurality of second prongs 44 extend in a proximal direction toward the handle 30. The bushing 128 is positioned between first and second discs 46, 54. More specifically, the bushing 128 is positioned between the bottom surface 52 of the first disc 46 and the top surface 58 of the second disc 54. In a preferred embodiment, the height 134 of the bushing 128 is dimensioned to separate or space apart the opposing first and second annular discs 46, 54. In an embodiment, the bushing 128 may be permanently affixed between opposing disc surfaces 52, 58. For example, the bushing 128 may be affixed between the first and second discs 46, 54 with an adhesive or a weld connection therebetween. In addition, the bushing 128 may be an extension of the first or second disc 46, 54 such that the bushing 128 and the first or second disc 46, 54 are of a one-piece body.

In a preferred embodiment, the height 134 of the bushing 128 can be adjusted to modify the position at which the opposing first and second prongs 42, 44 contact each other, thus modifying the frictional force therebetween. Therefore, by modifying the height 134 of the bushing 128 the area of contact between the first and second prongs 42, 44, can be adjusted. As a result, the amount of torque required to separate the opposing gears 38, 40 is modifiable. For example, reducing the bushing height causes the opposing first and second prongs 42, 44 to contact each other at a location closer to the respective proximal prong ends, thus requiring an increased amount of torque to separate the first and second gears 38, 40. Conversely, increasing the bushing height 134 causes the opposing first and second prongs 42, 44 to contact each other at a location closer to the respective distal prong ends, thus decreasing the amount of torque required to separate gears 38, 40, which therefore results in a decrease in the amount of torque imparted by the tool 10.

Once the second disc 54 is secured to the shank 24, the shank is positioned within the distal housing portion 20, as illustrated in FIG. 4. In a preferred embodiment, the distal housing portion 20 comprises a distal housing sidewall 142 extending proximately from an end wall 143 to define a distal housing cavity 144. As illustrated, the distal housing sidewall 142 extends circumferentially around and lengthwise along longitudinal axis A-A. A distal housing opening 146 resides in the end wall 143 and provides an opening for the shank distal end 28 to extend therethrough. In addition, the distal housing sidewall 142 comprises a sidewall thickness 148. In a preferred embodiment, sidewall thickness 148 may range from about 0.1 cm to about 10 cm. The sidewall thickness 148 provides a surface 150 that extends about perpendicular to longitudinal axis A-A on which the second annular disc 54 may be positioned. In a preferred embodiment, the second disc bottom surface 60 is positioned along the sidewall surface 150. In addition, the distal housing portion 20 may comprise an annular ridge 152 comprising an annular ridge sidewall 154 that extends proximally along longitudinal axis A-A and circumferentially around longitudinal axis A-A from surface 150. In a preferred embodiment, the second annular disc is positioned on the sidewall end surface 150 such that the second throughbore 64 of the second disc 54 is aligned with longitudinal axis A-A. More preferably, the second disc 54 is positioned within the perimeter that is defined by the annular ridge 152.

Once the shank 24 is positioned within the distal housing portion 20, the proximal housing portion 18 is connected thereto, thereby encasing the torque limiting mechanism 22 within the housing 16. In a preferred embodiment, the proximal and distal housing portions 18, 20 are connected with a series of pins (not shown) that connect the housing portions together. Alternatively, the proximal and distal housing portions 18, 20 can be connected with an adhesive material or by welding the two portions together. In a preferred embodiment, illustrated in FIGS. 2 and 4, the distal end surface of the proximal housing sidewall 112 is positioned in physical contact with ledge surface 156 that is positioned circumferentially about ridge 152 and extends perpendicular to longitudinal axis A-A and (FIG. 4). Once the proximal housing portion 18 is positioned in contact with the distal housing portion 20, the plurality of pins may be positioned through opening 158 which extends perpendicularly though the sidewall 112 of the proximal housing portion 18 and opening 160 which extends about perpendicular through ridge 152.

In a preferred embodiment, the respective prongs 42, 44 of the first and second gears 38, 40 are positioned in opposition such that at least one prong of the plurality of first prongs 42 is in physical contact with at least one prong of the plurality of second prongs 44. As a result of the physical contact therebetween, torque is imparted between the opposing prongs which causes both the first and second gears to rotate together which, in turn, causes the shank 24 to rotate about longitudinal axis A-A.

As illustrated in FIGS. 4 and 5A physical contact between the opposing prongs 42, 44 occurs when a portion of the opposing ramp surfaces 108A, 108B of the intermediate prong portion 74 of the first and second prongs 42, 44, respectively become in physical contact therebetween. As illustrated in FIG. 5A, the opposing ramp surfaces 108A, 108B are shown in physical contact with each other. Most preferably, the inflection location 110 of the respective first and second gear prongs 42, 44 are in physical contact with each other. Thus, as the first prongs 42 of the first gear 38 rotates about longitudinal axis A-A, a force is applied to the respective second prongs 44 of the second gear 40, thereby imparting a torque to the second gear 40 which causes it to rotate with the first gear 38. In a preferred embodiment, rotation of the handle portion 30 causes rotation of the second gear 40 thus, causing the shank 24 to rotate about longitudinal axis A-A. The torque limiting tool 10 of the present invention may be designed such that the shank 24 may rotate either in a clockwise or counterclockwise direction about rotational axis A-A.

However, when an amount of torque that exceeds a maximum limit is applied, the opposing first and second gears 38, 40 become disengaged. Specifically, the opposing ramp surfaces 108A, 108B ride along each other such that the respective prongs 42, 44 are no longer in physical contact with each other and, therefore, become disengaged. More specifically, the increasing amount of torque applied between the opposing first and second prongs 42, 44, causes at least a portion of either of the first or second prongs 42, 44 to flex in either a downwardly or upwardly direction, as the case may be, with respect to imaginary plane B-B. Continued application of the torque causes the other of the first or second prong 42, 44 to ride along the opposed ramp surface 108A, 108B of the intermediate portion 74 of the opposing prong 42, 44 toward the respective plateau portion until they physically separate. For example, as illustrated in FIG. 5B, second prong 44 is shown to be in downwardly flexed position as the ramp surface 108B of the intermediate prong portion 74 of the first prong 42 rides up the inclined ramp surface 108A of the intermediate portion 74 of the second prong 44. As the torque limit is reached, at least a portion of the second prong 44 thereof is deflected downward and away from imaginary plane B-B while the ramp surface 108B of the first prong 42 slides along the ramp surface 108A of the second prong 44 towards the prong plateau at the distal prong end 76. This movement continues until the prong plateaus 98 of the opposing first and second prongs 42, 44 become in a parallel orientation as illustrated in FIG. 5B. Further continued application of torque causes the surfaces of the opposing plateau portions 98 to separate, thereby disengaging the first and second gears 38, 40. Therefore, further rotational movement of the shank 24 about rotational axis A-A is prevented. For example, once a maximum torque has been exceeded, the ramp surface 108B of the first prong 42 rides along the respective ramp surface 108A of the intermediate portion 74 of the second prong 44. This continues until the respective first and second prong plateaus 98 become in about a parallel orientation. As a result, the opposing first and second prongs 42, 44 of the first and second discs 46, 54 disengage and separate.

While the preferred embodiments of the torque limiting tool and methods have been described in reference to the environment in which they were developed, they are merely illustrative of the principles of the inventions. Other embodiments and configurations may be devised without departing from the spirit of the inventions and the scope of the appended claims.

Thus, it can be seen that the present invention provides a torque limiting tool for tightening a threaded fastener, such as a screw, to a specific torque to thereby secure an orthopedic bone plate, and the like, to a bone fragment. Specifically, the torque limiting tool is constructed having first and second gears with respective prongs that physically engage each other. The amount of torque applied by the tool can be engineered based on the modulus of elasticity of the materials used to construct the gear prongs in addition to the amount of separation or spacing provided between the two gears.

What is claimed is:

1. A torque limiting tool, comprising:
   a) a housing comprising a proximal housing portion rigidly connected to a distal housing portion, the housing extending along a rotational axis;
   b) a torque limiting mechanism disposed within the housing, the torque limiting mechanism comprising:
      i) a first disc rigidly connected to the proximal housing portion;
      ii) a second disc spaced from the first disc;
      iii) at least one first prong flexuraly extending from the first disc to a first prong distal portion facing the second disc; and
      iv) at least one second prong flexuraly extending from the second disc to a second prong distal portion facing the first disc,
      v) wherein the first and second prongs comprise respective first and second prong intermediate portions extending along first and second prong angles from the respective first and second discs to the first and second prong distal portions, and wherein the first and second prong angles are in opposition to each other; and
   c) a shank connected to the second disc and extending along the rotational axis to a shank distal end that is configured for removable attachment to a fastener,
   d) wherein, upon the application of a torque to the proximal housing portion, the first prong is contactable to the second prong as the shank rotates about the rotational axis until the torque exceeds a torque limit which causes the first and second prongs connected to their respective first and second discs to flex with respect to each other until the respective first and second prong distal portions move out of contact with each other so that the first disc connected to the proximal housing portion and the second disc connected to the shank are now rotatable relative to each other.

2. The torque limiting tool of claim 1, wherein the first and second prong angles range from about 40° to about 50°.

3. The torque limiting tool of claim 1, wherein the proximal housing portion comprises a handle.

4. The torque limiting tool of claim 1, wherein the first and second discs are annularly-shaped members.

5. The torque limiting tool of claim 1, wherein the second disc has a central opening residing along the rotational axis, the central opening having a keyed surface that matched a similarly keyed surface of the shank to thereby connect the shank to the second disc.

6. The torque limiting tool of claim 1, wherein the first prong distal portion comprises a first prong plateau that resides along a first imaginary plane aligned substantially perpendicular to the rotational axis, and wherein the second prong distal portion comprises a second prong plateau that resides along a second imaginary plane aligned substantially perpendicular to the rotational axis, and wherein the first imaginary plane is a first distance from the first disc and the second imaginary plane is a second distance from the second disc, the first and second distances each ranging from about 0.1 cm to about 10 cm.

7. The torque limiting tool of claim 1, wherein the upper torque limit ranges from about 0.007 N-m to about 122 N-m.

8. The torque limiting tool of claim 1, wherein the first and second discs are composed of a material selected from the group consisting of a polymeric material, a metallic material, a ceramic material, and combinations thereof.

9. The torque limiting tool of claim 1, wherein at least the first and second prongs are composed of a material having a modulus of elasticity ranging from about 0.01 GPa to about 10 GPa.

10. The torque limiting tool of claim 1, wherein at least the first and second prongs are composed of a material having a modulus of elasticity ranging from about 0.5 GPa to about 5 GPa.

11. An orthopedic kit comprising the torque limiting tool of claim 1, an orthopedic implant, and at least one fastener.

12. The torque limiting tool of claim 1, wherein the first and second discs have a respective plurality of first and second prongs spaced circumferentially about the rotational axis.

13. A torque limiting tool, comprising:
   a) a housing comprising a proximal housing portion comprising a handle, the proximal housing portion being rigidly connected to a distal housing portion, wherein the housing extends along a rotational axis;
   b) a torque limiting mechanism disposed within the housing, the torque limiting mechanism comprising:
      i) a first disc rigidly connected to the proximal housing portion;
      ii) a second disc spaced from the first disc;
      iii) at least one first prong flexuraly extending from the first disc to a first prong distal portion facing the second disc; and
      iv) at least one second prong flexuraly extending from the second disc to a second prong distal portion facing the first disc,
      v) wherein from a perspective looking along the rotational axis from the first housing portion to the second housing portion, the at least one first prong angles in one of a clockwise or counterclockwise direction and the second prong angles in the other of the clockwise or counterclockwise direction; and
   c) a shank connected to the second disc and extending along the rotational axis to a shank distal end that is configured for removable attachment to a fastener,
   d) wherein, upon the application of a torque to the proximal housing portion, the first prong is contactable to the second prong as the shank rotates about the rotational axis until the torque exceeds a torque limit which causes the flexural connection of at least one of the first and second prongs to their respective first and second discs to flex with respect to each other until the respective first and second prong distal portions move out of contact with each other so that the first disc connected to the proximal housing portion and the second disc connected to the shank are now rotatable relative to each other.

14. The torque limiting tool of claim 13, wherein the second disc has a central opening residing along the rotational axis, the central opening having a keyed surface that matched a similarly keyed surface of the shank to thereby connect the shank to the second disc.

15. The torque limiting tool of claim 13, wherein the first and second discs are annularly-shaped members.

16. The torque limiting tool of claim 13, wherein the first prong distal portion comprises a first prong plateau that resides along a first imaginary plane aligned substantially perpendicular to the rotational axis, and wherein the second prong distal portion comprises a second prong plateau that resides along a second imaginary plane aligned substantially perpendicular to the rotational axis, and wherein the first imaginary plane is a first distance from the first disc and the second imaginary plane is a second distance from the second disc, the first and second distances each ranging from about 0.1 cm to about 10 cm.

17. The torque limiting tool of claim 13, wherein the upper torque limit ranges from about 0.007 N-m to about 122 N-m.

18. The torque limiting tool of claim 13, wherein the first and second discs are composed of a material selected from the group consisting of a polymeric material, a metallic material, a ceramic material, and combinations thereof.

19. The torque limiting tool of claim 13, wherein at least the first and second prongs are composed of a material having a modulus of elasticity ranging from about 0.01 GPa to about 10 GPa.

20. The torque limiting tool of claim 13, wherein at least the first and second prongs are composed of a material having a modulus of elasticity ranging from about 0.5 GPa to about 5 GPa.

21. An orthopedic kit comprising the torque limiting tool of claim 13, an orthopedic implant, and at least one fastener.

22. The torque limiting tool of claim 13, wherein the first and second discs have a respective plurality of first and second prongs spaced circumferentially about the rotational axis.

23. A torque limiting tool, comprising:
a) a housing comprising a proximal housing portion rigidly connected to a distal housing portion, the housing extending along a rotational axis;
b) a torque limiting mechanism disposed within the housing, the torque limiting mechanism comprising:
  i) a first disc rigidly connected to the proximal housing portion;
  ii) a second disc;
  iii) at least one first prong flexuraly extending from the first disc to a first prong distal portion facing the second disc;
  iv) at least one second prong flexuraly extending from the second disc to a second prong distal portion facing the first disc;
  v) a bushing having a bushing height positioned between and in contact with the first and second discs along the rotational axis, wherein the bushing height is less than the combined distances of the first disc to the first prong distal portion and the second disc to the second prong distal portion; and
c) a shank connected to the second disc and extending along the rotational axis to a shank distal end that is configured for removable attachment to a fastener,
d) wherein, upon the application of a torque to the proximal housing portion, the first prong is contactable to the second prong as the shank rotates about the rotational axis until the torque exceeds a torque limit which causes the flexural connection of at least one of the first and second prongs to their respective first and second discs to flex with respect to each other until the respective first and second prong distal portions move out of contact with each other so that the first disc connected to the proximal housing portion and the second disc connected to the shank are now rotatable relative to each other.

24. The torque limiting tool of claim 23, wherein a proximal shank end is rigidly connected to both the bushing and the second disc.

25. The torque limiting tool of claim 23, wherein the first and second discs are annularly-shaped members.

26. The torque limiting tool of claim 23, wherein the second disc has a central opening residing along the rotational axis, the central opening having a keyed surface that matched a similarly keyed surface of the shank to thereby connect the shank to the second disc.

27. The torque limiting tool of claim 23, wherein the first prong distal portion comprises a first prong plateau that resides along a first imaginary plane aligned substantially perpendicular to the rotational axis, and wherein the second prong distal portion comprises a second prong plateau that resides along a second imaginary plane aligned substantially perpendicular to the rotational axis, and wherein the first imaginary plane is a first distance from the first disc and the second imaginary plane is a second distance from the second disc, the first and second distances each ranging from about 0.1 cm to about 10 cm.

28. The torque limiting tool of claim 23, wherein the upper torque limit ranges from about 0.007 N-m to about 122 N-m.

29. The torque limiting tool of claim 23, wherein the first and second discs are composed of a material selected from the group consisting of a polymeric material, a metallic material, a ceramic material, and combinations thereof.

30. The torque limiting tool of claim 23, wherein at least the first and second prongs are composed of a material having a modulus of elasticity ranging from about 0.01 GPa to about 10 GPa.

31. The torque limiting tool of claim 23, wherein at least the first and second prongs are composed of a material having a modulus of elasticity ranging from about 0.5 GPa to about 5 GPa.

32. An orthopedic kit comprising the torque limiting tool of claim 23, an orthopedic implant, and at least one fastener.

33. The torque limiting tool of claim 23, wherein the first and second discs have a respective plurality of first and second prongs spaced circumferentially about the rotational axis.

* * * * *